US010652674B2

(12) United States Patent
Lederman

(10) Patent No.: US 10,652,674 B2
(45) Date of Patent: May 12, 2020

(54) HEARING ENHANCEMENT AND AUGMENTATION VIA A MOBILE COMPUTE DEVICE

(71) Applicant: Jon Lederman, Moorestown, NJ (US)

(72) Inventor: Jon Lederman, Moorestown, NJ (US)

(*) Notice: Subject to any disclaimer, the term of this patent is extended or adjusted under 35 U.S.C. 154(b) by 0 days.

(21) Appl. No.: 15/947,635

(22) Filed: Apr. 6, 2018

(65) Prior Publication Data
US 2018/0227682 A1 Aug. 9, 2018

(51) Int. Cl.
H04R 25/00 (2006.01)
H04R 29/00 (2006.01)
A61B 5/12 (2006.01)
H04R 25/04 (2006.01)
H04M 1/60 (2006.01)
H04M 1/725 (2006.01)
A61B 5/00 (2006.01)

(52) U.S. Cl.
CPC .......... H04R 25/554 (2013.01); A61B 5/123 (2013.01); H04M 1/6066 (2013.01); H04R 25/04 (2013.01); H04R 25/70 (2013.01); A61B 5/6898 (2013.01); H04M 1/72527 (2013.01); H04R 25/505 (2013.01); H04R 2420/07 (2013.01); H04R 2499/11 (2013.01)

(58) Field of Classification Search
CPC ............................... H04R 29/00; H04R 25/00
USPC .................................... 381/60, 312, 316, 320
See application file for complete search history.

(56) References Cited

U.S. PATENT DOCUMENTS

| 7,529,545 | B2 | 5/2009 | Rader et al. | |
|---|---|---|---|---|
| 8,135,138 | B2* | 3/2012 | Wessel | H04R 25/70 381/60 |
| 8,437,479 | B2* | 5/2013 | Ganter | A61B 5/123 381/314 |
| 9,031,247 | B2* | 5/2015 | Shennib | H04R 25/70 381/60 |
| 9,185,497 | B2 | 11/2015 | Liaw et al. | |

(Continued)

FOREIGN PATENT DOCUMENTS

WO    WO 2008/138349    11/2008

OTHER PUBLICATIONS

"AirPods as Hearing Aids, Is This Truly Possible," Audiology Worldnews, Aug. 22, 2017, 8 pages.

(Continued)

Primary Examiner — Suhan Ni

(57) ABSTRACT

The presently disclosed subject matter includes a mobile compute device configure to produce a set of audiological assessment data based on a set of stimulus signals presented to a user via a source device and a set of response signals provided as a response to the set of stimulus signals. The mobile compute device identifies a personal audiological profile of the user at least based on a psychoacoustic model and the set of audiological assessment data. The mobile compute device builds a digital signal processing model including a set of audio digital signal processing functions. The mobile compute device executes the digital signal processing model to produce an output audio signal in response to an input audio signal received from the source device, the output audio signal is based on a modified version the input audio signal. The mobile compute device transmits the output audio signal via the source device.

18 Claims, 11 Drawing Sheets

(56) References Cited

U.S. PATENT DOCUMENTS

| | | |
|---|---|---|
| 9,338,555 B1 | 5/2016 | Oxford |
| 2015/0281853 A1 | 10/2015 | Eisner et al. |
| 2016/0241972 A1 | 8/2016 | Gobeli et al. |
| 2017/0061978 A1 | 3/2017 | Wang et al. |

OTHER PUBLICATIONS

Baig, "A new feature turns Apple AirPods into impromptu hearing aids. We tried it," Jun. 26, 2018, 3 pages, https://www.usatoday.com/story/tech/talkingtech/2018/06/26/apple-airpods-can-sub-hearing-aid-if-youre-running-ios-12/735686002/.

Bauml et al., "Uniform Polyphase Filter Banks for Use in Hearing Aids: Design and Constraints," EUSIPCO 2008, Aug. 2008, 5 pages.

Brennan et al., "A Flexible Filterbank Structure for Extensive Signal Manipulations in Digital Hearing Aids," IEEE 1998, 4 pages.

Chen et al., "Deep Attractor Network for Single-Microphone Speaker Separation," IEEE 2017, 5 pages.

Devis et al., "Multirate and Filterbank Approaches in Digital Hearing Aid Design: A Review," IOP Conf. Series: Materials Science and Engineering, 396, 2018, 9 pages.

Dhanya et al., Reconfigurable Filter Bank Structures for Hearing Aid Applications, International Journal of Pure and Applied Mathematics, vol. 118, No. 11, 2018, 805-812, 8 pages.

EarMachine, 4 pages http://www.earmachine.com/.

Fennex Launches Hearing App for Use with Apple AirPods, Aug. 18, 2017, 6 pages.

Foulad et al., "Automated Audiometry Using Apple iOS-Based Application Technology," Aug. 20, 2013, 3 pages, https://journals.sagepub.com/doi/abs/10.1177/0194599813501461?journalCode=otoj&.

Han et al., "Learning Spectral Mapping for Speech Dereverberation and Denoising," IEEE/ACM Transactions on Audio, Speech, and Language Processing, vol. 23, No. 6, Jun. 2015, 11 pages.

hearingOS—the iPhone hearing app, 4 pages, https://www.hearingos.com.

The International Hearing Aid Research Conference 2000, Aug. 2000, 75 pages.

Kates, "Principles of Digital Dynamic-Range Compression," Trends Amplif., 2005 Spring; 9 (2): 45-76, 45 pages.

Levitt, "A Historical Perspective on Digital Hearing Aids: How Digital Technology Has Changed Modern Hearing Aids," Trends in Amplification, vol. 11, No. 1, Mar. 2007, 18 pages.

Metz, "How Your Apple Wireless Earbuds Could Double as Hearing Aids," Aug. 14, 2017, 12 pages, https://www.technologyreview.com/s/608597/how-your-apple-wireless-earbuds-could-double-hearing-aids/.

Petralex Hearing Aid App, 13 pages.

Regalia, et al., "Tree-Structured Complementary Filter Banks Using All-Pass Sections," IEEE. Transactions on Circuits and Systems, vol. Cas-34, No. 12, Dec. 1987, 15 pages.

Wang, "Deep Learning Reinvents the Hearing Aid," IEEE Spectrum, Dec. 6, 2016, 9 pages.

* cited by examiner

HEARING ENHANCEMENT AND AUGMENTATION VIA A MOBILE COMPUTE DEVICE

TECHNICAL FIELD

This disclosure relates to hardware- and software-based systems for improvements in audio signals and hearing enhancement techniques. In particular, the present disclosure is related to hearing aid device devices, hearing enhancement devices and hearing augmentation devices.

BACKGROUND

Health professionals perform hearing assessments to obtain multiple hearing measures from individuals to assess the presence of suffering from hearing impairments. Health professionals customize and fit hearing aid devices to correct individual-specific hearing impairments based on measurements obtained through these assessments. Often times these assessments fail to measure the full scope of human auditory perception. Moreover, individuals with hearing impairments have to recurrently visit health professionals to have their hearing aid devices adjusted or calibrated because such hearing devices tend to include dedicated hardware and software with multiple operation parameters that cannot be configured or re-configured in a straightforward manner.

Therefore, a need exists for hearing aid devices that can be customized by individuals with hearing impairments without the intervention of health care professionals, and for devices that are improved to produce optimal sound signals based on robust and reliable audiological assessments including the full scope of human auditory perception.

DETAILED DESCRIPTION

Figure 1:
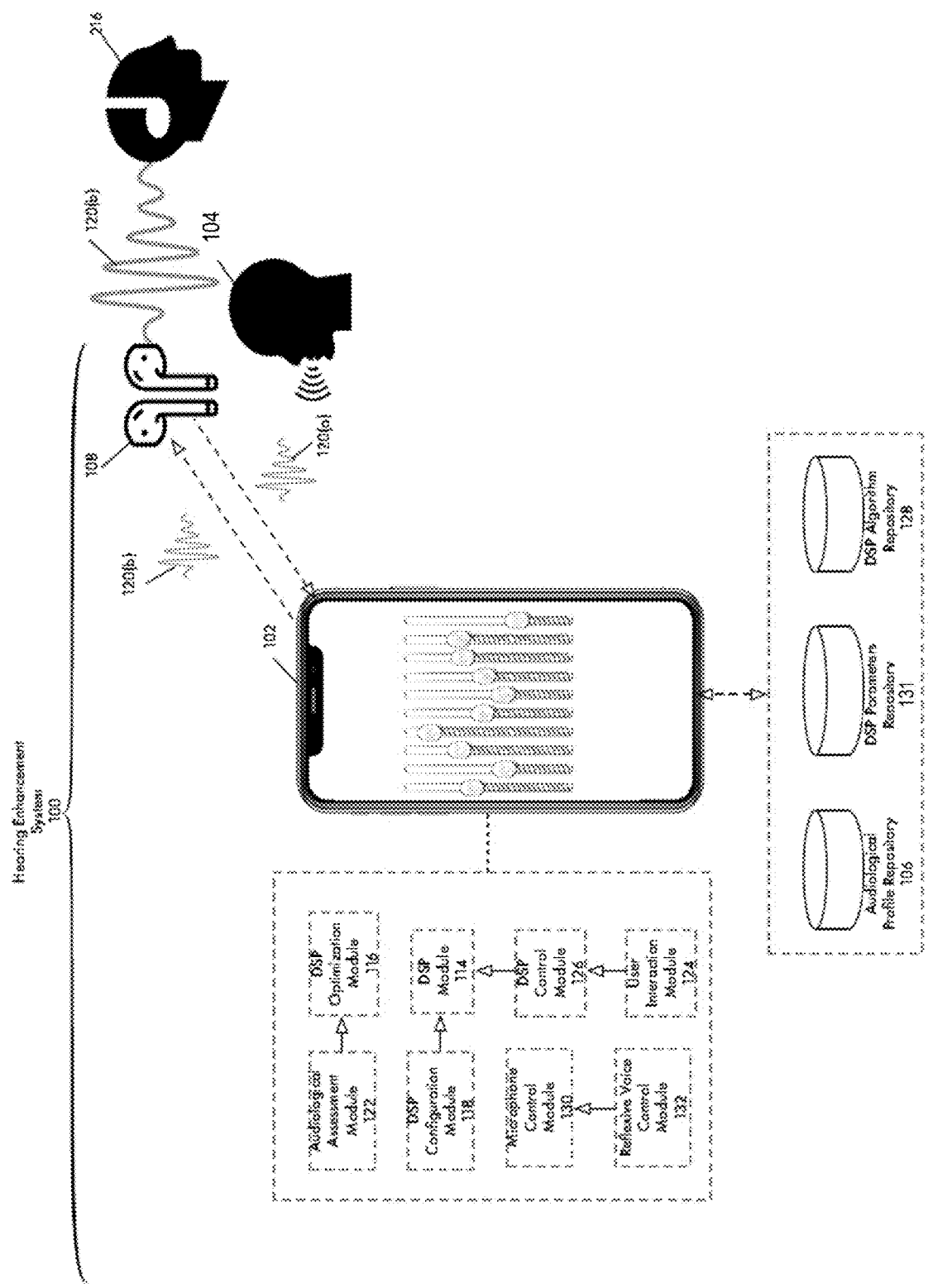
FIG. 1 is a diagram of a hearing enhancement system, according to an embodiment.

The detailed description set forth below is intended as a description of various configurations of the subject technology and is not intended to represent the only configurations in which the subject technology may be practiced. The appended drawings are incorporated herein and constitute a part of the detailed description. This description includes specific details for the purpose of providing a thorough understanding of the subject technology. It will be clear and apparent that the subject technology is not limited to the specific details set forth herein and may be practiced without these specific details. In some instances, well-known structures and components are shown in block diagram form.

The terms "computer", "processor", "computer processor", "compute device" or the like should be expansively construed to cover any kind of electronic device with data processing capabilities including, by way of non-limiting example, a digital signal processor (DSP), a microcontroller, a field programmable gate array (FPGA), an application specific integrated circuit (ASIC), or any other electronic computing device comprising one or more processors of any kind, or any combination thereof.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

Hearing aid devices are often customized according to hearing measurements of an individual so as to correct or compensate for specific audiological impairments. Generally, an individual is required to seek an audiological assessment from a trained health professional (e.g., audiologist) and based on a series of audiological measurements a hearing aid device can be fitted to the individual. An audiogram is perhaps the most conventional way to represent an audiological assessment. An audiogram can include measures an individual's ability to hear various pure tone (sinusoidal) frequencies at various loudness levels (amplitudes) across the frequency spectrum. This type of audiological assessment is often referred to as a minimum threshold test. The minimum threshold test is designed to detect the minimum amplitude at which an individual can hear a particular frequency. Audiologists applying conventional methods can also detect an individual's sensitivity to discomfort when such an individual is exposed to various pure tone frequencies at various amplitudes. One or both of these measurements (minimum threshold and discomfort level) of various tones can then be analyzed by an audiologist to customize or fit a hearing aid device to the needs of an individual.

Conventional hearing aid devices include multiple controllable or adjustable parameters whose settings can be selected by an audiologist to compensate for identified impairments based on a measured audiogram. In addition, an audiologist can conduct an interactive session with an individual by tuning and tweaking various controls or parameters of a hearing aid device during the fitting process so that the settings of the hearing aid device are optimal for the user.

Conventional assessment and fitting methods such as those described above have significant drawbacks. First, they require the involvement of a trained audiologist or other health professional, which can dissuade some individuals with hearing impairments from seeking out help. Further, the conventional method of measuring an audiogram by performing a minimum threshold test and possibly a discomfort test fails to measure the full scope of human auditory perception, as it is a rather superficial and subjective test. Moreover, good quality hearing aid devices are typically expensive and may be unaffordable to the individual already suffering from an impairment. Even individuals that can afford high-end hearing aid devices can be deterred because of concerns for negative stereotyping that can sometimes be associated with the use of such devices. In light of the various drawbacks with conventional hearing aid devices and the associated audiological assessments, many people who suffer from hearing loss simply decide not to be fitted for a hearing aid device and instead live with various degrees of inconvenience and annoyance associated with hearing impairments.

Recent legislation has provided for the selling of over-the-counter ("OTC") hearing aid devices without the requirement for the involvement of a trained health professional but only for hearing loss that is mild to moderate (i.e., hearing loss beyond the moderate level such as severe/profound sill requires an audiologist's involvement). Although OTC sound amplification products have been available for a number of years, the recent legislation provides for OTC sales using the label "hearing aid device" but only for individuals with mild to moderate hearing loss. Hearing aid devices targeted for individuals with hearing loss beyond moderate levels such as severe to profound is prohibited by law.

It is appreciated that some modern mobile compute devices such as smartphones, tablets, laptops, and other similar mobile or stationary compute devices are ubiquitous and feature high computational power. Among other capabilities, these mobile compute devices offer significant capabilities for multimedia experiences including audio and video. It is also appreciated that mobile compute devices such as the Apple® iPhone® and Android® devices provide high-fidelity stereo digital audio that rivals or exceeds the performance of high-end audio equipment. Likewise, it is appreciated that the computational capabilities of some mobile compute devices and other stationary compute devices can be leveraged for digital signal processing ("DSP") whereby audio data can be transformed in multiple ways.

The present disclosure describes techniques for effectively improving commodity mobile compute devices such as the Apple® iPhone® and/or Android® devices, or other suitable compute devices to function as effective hearing enhancement/augmentation devices whereby these improved devices afford capabilities that surpass those of dedicated hearing aid devices. Mobile compute devices can be improved to function as hearing enhancement or augmentation device and/or as replacement for dedicated or customized hearing aid devices. In particular mobile compute devices can be improved with software or processor executable instructions, hardware, and/or combinations of hardware and software to function as hearing enhancement or augmentation systems to process and refine speech signals or other audio to meet the needs of, for example, individuals with hearing impairments. Mobile compute devices coupled with the high-end audio technological improvements can improve the quality of sound signals produced by conventional hearing aid devices, increase the usability of hearing aid devices by in some instances, eliminating or reducing the need to consult an audiologist, improve the quality of sound signals while decreasing costs.

Smartphones improved to function as a hearing aid device or hearing augmentation device can produce audio signals of quality superior to that of conventional and dedicated hearing aid devices. For instance, modern smartphones such as the iPhone® and Android® have powerful CPUs and/or dedicated DSP hardware specifically designed for audio processing. In addition, these devices generally include multiple high-quality microphones and playback apparatus capable of recording high fidelity audio and playing audio back to a user.

FIG. 1 depicts a hearing enhancement system according to one embodiment of the present disclosure. One or more speakers e.g., speaker 104 generate a voice signal that is received by one or more microphones (not shown in FIG. 1) on transceiver device 108 (as unprocessed audio 120(a)) and/or one or more microphones (not shown in FIG. 1) on processing device 102 and processed by processing device 102 to generate processed audio 120(b). Processed audio 120(b) is then played back to user 216 on transceiver device 108.

As shown in FIG. 1, hearing enhancement system 100 can include processing device 102, audiological profile repository 106, DSP parameters repository 131, DSP algorithm/model repository 128, and transceiver device 108. An operation of hearing enhancement system 100 will now be described. According to one embodiment, processing device 102 can be any device capable of performing digital processing of data. In particular, according to some embodiments, processing device 102 can be any device further comprising a CPU, dedicated DSP, or other suitable processing device. According to some embodiments, processing device 102 can be a mobile compute device such as a smartphone for instance, an Apple® iPhone® or an Android® device. According to other embodiments, processing device 102 can be a device such as a desktop computer or laptop.

Processing device 102 can receive and transmit audio data to and from transceiver device 108. In particular, processing device 102 and transceiver device 108 can exchange digital audio data either in raw or encoded format. Thus, as shown in FIG. 1 processing device 102 can receive unprocessed audio 120(a) from transceiver device 108. Processing device 102 can then process unprocessed audio 120(a) to generate processed audio 120(b), which processing device 102 can then transmit back to transceiver device 108 for playback. As will be described below, according to alternative embodiments, unprocessed audio 120(a) can be received at processing device 102 directly via, for example, an embedded microphone or auxiliary microphone. Further, according to some embodiments, transceiver device 108 can function as a playback device and can receive processed audio 120(b) via a wireless or wired connection. According to some embodiments, a wireless connection between processing device 102 and transceiver device 108 can utilize radio bandwidth frequencies. According to other embodiments, processing device 102 and transceiver device 108 can exchange data over an optical connection using optical frequencies. For the purposes of the present discussion, it can be assumed that transceiver device 108 can perform recording and playback functions and exchanges data with processing device 102 wirelessly using radio frequencies. However, the aforementioned alternative embodiments are also possible.

Transceiver device 108 can include any device capable of recording an acoustic audio signal and playing back an acoustic audio signal. Thus, according to some embodiments, and as described in more detail below, transceiver device 108 can further include one or more microphones and one or more speakers. According to some embodiments, in which transceiver device 108 includes multiple microphones, it can perform a beamforming function to direct the beam pattern of detected acoustic signals. According to one embodiment, transceiver device 108 can be wireless earbuds that can utilize any type of wireless protocol such as Bluetooth®. For example, transceiver device 108 can be the Apple® AirPods®, which include an in-ear speaker for playback of audio and a microphone for audio capture. According to an alternative embodiment, transceiver device 108 can include wired earbuds that include one or more microphones and one more speakers, for example the Apple® EarPods®.

According to one embodiment, the playback function of wireless earbuds can be used while the record functionality can be provided by processing device 102. For instance, if transceiver device 108 is the Apple® AirPods®, according to some embodiments, the playback capability of the AirPods® is used while the record functionality can be provided by the built-in microphone(s) on the Apple® iPhone® alone. Other combinations can be similarly implemented in transceiver device 108. For example, an external microphone can be used in combination with processing device 102.

According to one embodiment, transceiver device 108 can provide stereo recording and playback capabilities as well as monophonic recording and playback capabilities. According to alternative embodiments, transceiver device 108 can exchange any number of audio channel data with processing device 102. For example, according to one embodiment, transceiver device 108 can include an arbitrary number of microphones and can thereby exchange audio data detected by each respective microphone with processing device 102. Further, as will be described in detail below, transceiver device 108 can exchange stereo (two channels) data or monophonic data with processing device 102. As will be described in detail below, processing device 102 can perform processing of monophonic, stereo or audio data comprising any number of audio channels.

According to some embodiments, rather than receiving unprocessed audio 120(*a*) from transceiver device 108, processing device 102 can receive unprocessed audio 120(*a*) directly from a microphone embedded with or coupled to processing device 102, which can then be transmitted to transceiver device 108.

It will be understood that processing device 102 and transceiver device 108 can operate in a streaming configuration whereby unprocessed audio 120(*a*) captured on transceiver device 108 is continuously streamed in a series of audio blocks to processing device 102, where it is processed to generate processed audio 120(*b*) and then streamed back to transceiver device 108 for playback. As discussed below, the nature of the streaming process between processing device 102 and transceiver device 108 is an important factor in ensuring the quality of experience of a user listening to processed audio 120(*b*).

According to some embodiments, digital audio transmitted between processing device 102 and transceiver device 108 can be encoded using any audio compression algorithm such as AAC ("Advanced Audio Coding"), Opus, or other suitable audio compression algorithm.

An operation of processing device 102 will now be described. For purposes of the present discussion, it is sufficient to recognize that processing device 102 can include any device that can perform processing of digital data. Thus, according to one embodiment, processing device 102 can further include a Central Processing Unit (CPU) and a memory or non-transitory computer-readable medium (not shown in FIG. 1). Processing device 102 can further include an output apparatus such as a screen or touchscreen for displaying text and graphical information. An operating system associated with processing device 102 can provide a framework and API ("Application Programming Interface") for generating arbitrarily complex graphical interactive environments so that users of processing device 102 can interact with sound, audiological data, DSP control, and parameters in a programmable/configurable and flexible manner. Processing device 102 can execute via its associated CPU an operating system that allows a user to interact with processing device 102. In addition, processing device 102 can further include user interaction ("UP") hardware and software to facilitate user interaction with processing device 102, for example, via a haptic signal, keyboard, voice, or other input modalities. Further details regarding various embodiments of processing device 102 are described below.

Referring again to FIG. 1, processing device 102 can include any number of components or components, for example, those shown in FIG. 1, comprising audiological assessment component 122, DSP optimization component 116, DSP configuration component 118, DSP component 114, DSP control component 126, user interaction component 124, microphone control component 130, and reflexive voice control component 132. According to some embodiments, the aforementioned components or components can include software components that can execute on a CPU associated with processing device and thus, include logical entities and data structures. However, according to alternative embodiments, processing device 102 can further include specialized hardware for performing various functions represented by these components.

Further, although FIG. 1 depicts the components as distinct logical blocks, it will be appreciated that the functionalities associated with these entities can be combined in any fashion including, for example, a single monolithic software application or single hardware component. On the other hand, according to alternative embodiments, additional components can be introduced, which can perform the logical functionalities depicted in alternative arrangements.

A high-level description of audiological assessment component 122, DSP optimization component 116, DSP configuration component 118, DSP component 114, DSP control component 126, user interaction component 124, microphone control component 130, and reflexive voice control component 132 and their interoperations will now be provided according to one embodiment. Detailed embodiments of the depicted components and/or components are described below. As previously mentioned, according to one embodiment, processing device 102 can execute DSP component 114, DSP optimization component 116, DSP configuration component 118, audiological assessment component 122, DSP control component 126, user interaction component 124, microphone control component 130, and/or reflexive voice control component, each of which can include a software component or component executed on a CPU or other suitable processor and/or compute device.

Audiological assessment component 122 can perform various processes for determining the audiological profile of an individual/user who might wish to use hearing enhancement system 100. According to one embodiment, and as described in more detail below, audiological assessment component 122 can provide a framework for generating a plurality of stimuli and detecting an associated set of responses from an individual. The combination of stimuli/responses can include what is referred to herein as audiological assessment data and a person's audiological profile can be determined from such audiological assessment data.

According to one embodiment, audiological assessment component 122 can perform various functions for determining an audiological profile of an individual and maintaining the audiological profile in a persistent storage such as a database at, for example, audiological profile repository 106. As used herein, an audiological profile can be produced from a set of response data provided by an individual and received by audiological assessment component 122 in response to a set of stimuli presented to the individual by audiological assessment component 122. It will be appreciated that there need not be a one-to-one correspondence between stimuli and response data as part of an audiological assessment.

DSP optimization component 116 can generate DSP parameters and determine a DSP algorithm or model based on an audiological profile determined by audiological response component 122. In some instances, the DSP algorithm or model can be retrieved from DSP repository 128. In some implementations, DSP repository 128 can be implemented at a local memory included in processing device 102. In some other implementations, DSP repository can be implemented at a cloud-based storage device and accessed by processing device 102 via the Internet. DSP optimization component 116 can perform various processes for transforming audiological assessment data into an associated set of DSP parameters with respect to pre-specified DSP models, for instance a pre-specified DSP model stored in DSP algorithm repository 128. According to alternative embodiment, DSP optimization component 116 can also determine both a DSP algorithm and model and associated DSP parameters for that algorithm or model based upon audiological assessment data.

DSP component 114 can provide audio DSP functions for transforming an input audio signal into an output audio signal that has been processed to personalize customize and/or adapt the audio for a particular user. The structure of an example DSP component 116 is described in detail below. According to one embodiment, DSP component 116 can include a DSP algorithm or model and a set of associated DSP parameters. As will be discussed below, a DSP algorithm or model can include a series of instructions for specifying a transformation of unprocessed audio 120(a) into processed audio 120(b). A DSP algorithm or model can be expressed as a block diagram of various processing blocks either in the time domain or frequency domain and/or as a set of associated mathematical transformations characterizing those processing blocks.

DSP parameter repository 131 stores DSP parameters, which can be associated with a DSP algorithm or model, DSP parameters, can include variables, numerical quantities, ordinal values and other suitable data values specifying settings that are associated with a DSP algorithm or model. For example, according to one embodiment, in the scenario of a simple audio equalizer with a set number of equalization bands, a single DSP parameter can be associated with each frequency band indicating a particular boost value to be applied to that respective band. Similarly, with respect to a DSP algorithm or model that can include an audio compression algorithm or model, DSP parameters can specify various values corresponding to compression attributes such as threshold, attack, release, and compression ratio among others.

According to one embodiment DSP component 114 can include a framework for audio processing that can allow specification of a DSP algorithm or model and associated parameters via a set of audio DSP primitive pre-programmed functions stored at, for example, DSP algorithm repository 128 that can be arranged to include more complex DSP algorithms. The parameters for such models or algorithms are selected or determined such that, adjustment of such parameters is influenced by a detected or selected audiological profile so as to compensate for an individual audiological impairments.

Audiological Assessment Component

Figure 2:
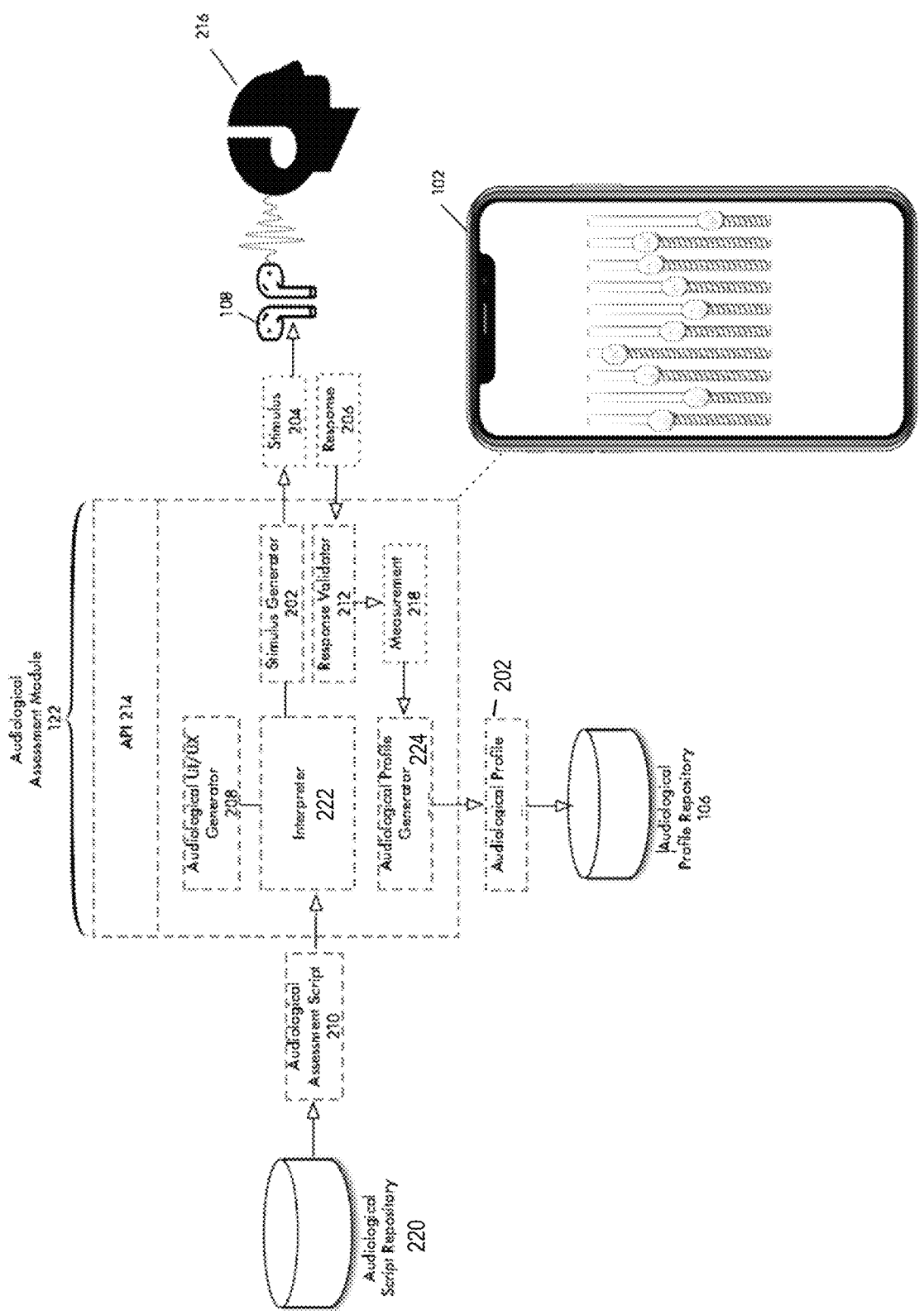
FIG. 2 is a block diagram depicting a structure and function of an audiological assessment component, according to an embodiment.

FIG. 2 is a block diagram depicting a structure and function of an audiological assessment component or component 122 according to one embodiment of the present disclosure. As shown in FIG. 2, according to one embodiment, audiological assessment component 122 can further include an Application Programming Interface (API) 214, interpreter 222, audiological User Interface (UI) and/or User Experience (UX) generator 208, response validator 212, stimulus generator 202 and audiological profile generator 224 and measurement 218.

A high-level operation of audiological assessment component 122 will now be provided with more details below. According to one embodiment, audiological assessment component 122 can perform an audiological assessment of user 216 to generate one or more audiological profiles 202 associated with user 216. As used herein, an "audiological profile" can include any data or information based on one or more measurements of an audiological perception or acuity of user 216. In particular, according to one embodiment, audiological assessment component 122 can generate one or more stimuli 204, which are provided to user 216. In turn, user 216 can generate one or more responses 206 based on individual's perception of stimuli 204, which can then be analyzed or transformed by response validator 212 into associated measurement(s) 218. One or more measurements 218 can then be received by audiological profile generator 224, which generates audiological profile 202.

According to one embodiment, stimulus 204 can include any type of audio transformed into an acoustic signal by transceiver device 108. For example, according to one embodiment, stimulus 204 can include a digital representation of an audio signal, for example, Pulse Code Modulation (PCM) samples. According to one example, as discussed below, audiological assessment component 122 can generate audio signals comprising pure-tones at various frequencies and associated amplitudes. Each pure-tone can be an audio signal having a frequency content comprising a single frequency. According to alternative embodiments, audiological assessment component 122 can generate more complex audio stimuli 204 such as, for example, a sweep of frequency components over some time.

According to some embodiments, in addition to generating audio stimuli 204, in performing an audiological assessment, audiological assessment component 122 can use audiological UI/UX generator 208 to generate other media, which can be presented to user 216 including images, animations, or other graphical representations or other UI elements, which can be displayed via processing device 102. Further, according to some embodiments, audiological assessment component 122 can combine various media types in a multimedia context, which are presented to user 216.

As previously noted, response 206 can be any action made by user 216 received by transceiver 108 (e.g., voice command) and/or a sensor embedded in processing device 102 (e.g., touchscreen) which can be transformed into a hearing measurement of user 216 processed in response to stimulus 204. In some instances, response 206 can be received from user 216 in a form or format that is further processed or transformed by processing device 102 to generate a hearing measurement and subsequently produce an audiological profile 202, which is stored in audiological profile repository 106. For instance, e, according to one embodiment, response 206 can be received in a raw format that is not directly indicative of an audiological measurement. For example, response 206 can be received from processing device 102 and include data indicating individual's interaction with a UI element, such as moving a slider to a new position or other interaction with a UI element display on the screen of processing device 102. Thus, processing device 102 can calculate or process the new slider position and based on the new slider position calculate an audiological measurement used thereafter to produce an audiological profile.

Response validator 212 can receive response 206 generated by individual and transform response 206 into an associated measurement 218. Measurement 218 can include, for example, any data comprising an audiological measurement. In particular, response validator 212 that can perform various validations and manipulations of response 206 to generate an associated audiological measurement 218, which is then provided to audiological profile generator 224, can receive response 206.

For example, according to one embodiment, user 216 can be presented with a User Interface (UI) element for controlling the amplitude of one or more sinusoidal pure-tone frequency audio waveforms generated by audiological assessment component 122 (e.g., stimuli 204). User 216 can also be presented with a UI element via audiological UI/UX generator 208 that allows user 216 to indicate or command adjustments of the amplitude of a tone, when the tone is barely audibly detectable (i.e., exceeds a minimum threshold of audibility for that user). In this context, the indication of the minimum threshold of audibility, for example, by touching the UI element is an example of a response 204 that can be detected by audiological assessment component 122. However, more sophisticated and complex examples of stimuli/response are enabled in other embodiments.

Continuing with this example, user 216 can move a slider shown as a graphical element on the screen of processing device 102 after receiving stimulus 204 to indicate the individual's ability to detect the pure-tone signal. The particular slider position can thereby include response 206. Response validator 212 can receive response 206 (i.e., the slider position) and convert the response into an appropriate audiological measurement, for example, converting the slider position to a respective decibel (dB) level and further perform various validation checks regarding the accuracy of the individual's response. Upon validation and upon performing appropriate transformations to audiological data, response validator 212 can then generate measurement 218.

According to some embodiments, audiological assessment component 122 can determine audiological profile 202 of user 216, which can then be stored in audiological profile repository 106 via an audiological assessment script 210 retrieved from audiological script repository 220. Audiological assessment script 210 can include a sequence of computer executable instructions or a process for performing an audiological assessment for generating a specific audiological profile 202. In particular, different types of audiological assessments can be performed depending on the particularities of a set of stimuli 204 that are to be presented to user 216. Interpreter 222 can interpret audiological assessment script 210. Audiological assessment script 210 can also specify various UI/UX elements to be generated/displayed during an audiological assessment. These UI/UX elements can be generated/rendered by audiological UI/UX generator 208 on the screen of processing device 102.

Example embodiments of data formats for audiological response data are described below as well as example embodiments of a structure and operation of audiological data repository 106. Further, although as depicted in FIG. 1, audiological data repository 106 is shown to be co-located with processing device 102, it will be understood that audiological data repository 106 can instead be coupled to a network such as a private network or public network e.g., the Internet, whereby processing device 102 can interact (i.e., store and retrieve data and perform other functions) with audiological data repository over a network connection.

DSP Optimization Component

Figure 3:
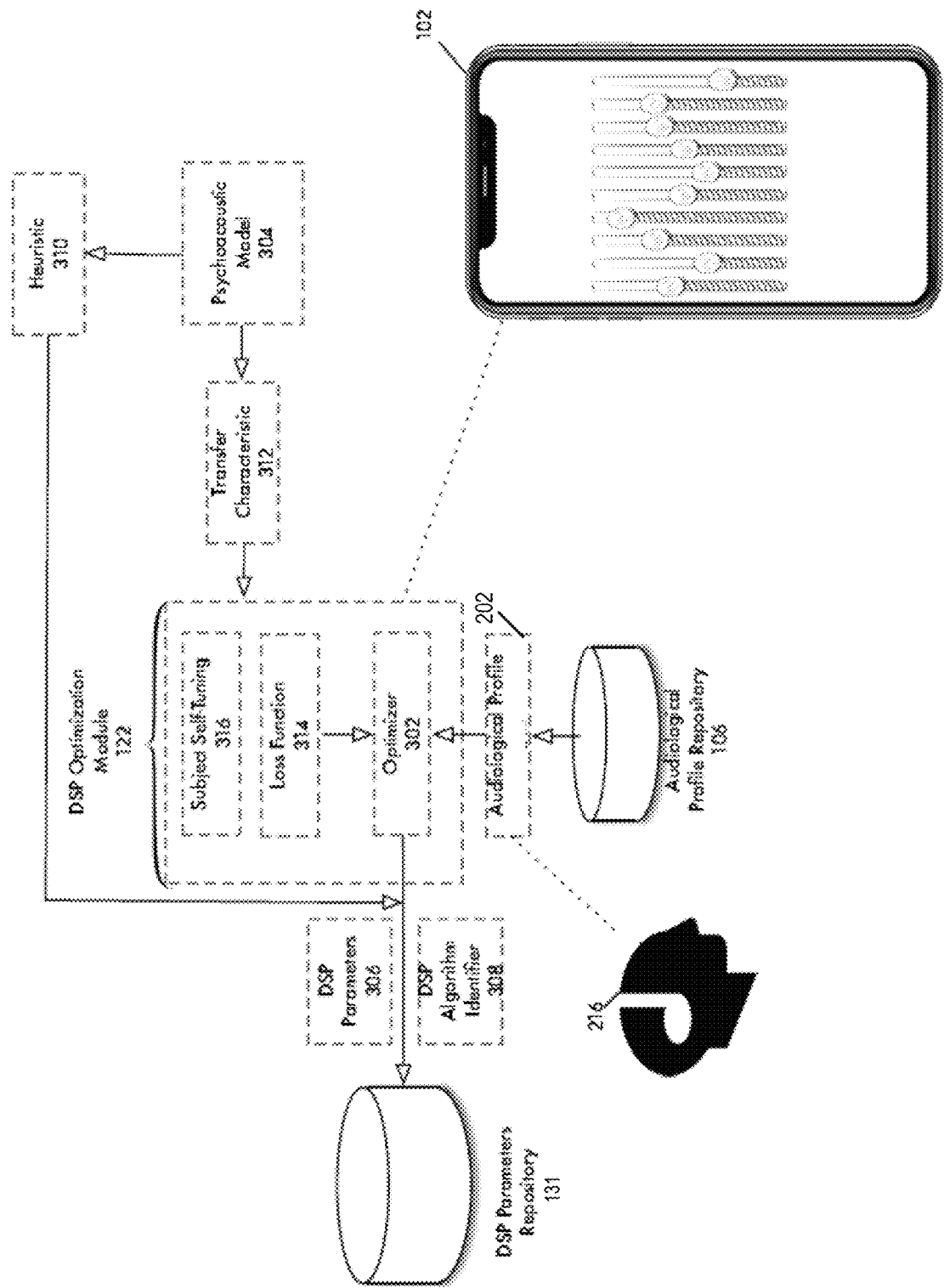
FIG. 3 is a block diagram depicting an operation of a digital signal processor (DSP) optimization component, according to an embodiment.

FIG. 3 is a block diagram depicting an operation of a DSP optimization component according to one embodiment of the present disclosure. As shown in FIG. 3, DSP optimization component 122 can further include optimizer 302, loss function 314 and individual self-tuning component 316. According to one embodiment, DSP optimization component 122 can use one or both of transfer characteristic 312 and heuristic 310 to determine an optimal DSP algorithm or model identifier 308 and associated DSP parameters 306 for user 216 based upon audiological profile 202 of user 216.

According to one embodiment, psychoacoustic model 304 includes descriptive information representing a model of the human auditory system with respect to speech discrimination. Psychoacoustic model 304 provides a representation of an individual's ability to hear/discriminate specific speech signal dependent on a particular audiological profile 202. Psychoacoustic model 304 can include a physiological model of the human auditory pathway or other type of suitable model.

Either or both, a heuristic 310 and a transfer characteristic 312 can be generated from psychoacoustic model 304. Heuristic 310 can be a set of rules or an executable program that maps audiological profile 202 to DSP parameters 306 and DSP algorithm or model identifier 308 based on psychoacoustic model 304. In particular, based on a set of measurements comprising audiological profile 202, heuristic 310 can provide a set of rules or guidelines for generating an associated DSP algorithm or model identifier 308 and DSP parameters 306.

For example, according to one embodiment, audiological profile 202 can include a set of minimum threshold measurements and discomfort level measurements associated with a set of frequencies. Each minimum threshold measurement can indicate a minimum level (loudness) at which user 216 can hear a particular pure tone frequency (pitch). Each discomfort level can indicate a maximum level tolerable by user 216 for a given pure frequency tone. Thus, the combination of a minimum threshold level and discomfort level can provide a range expressed in, for example, decibels defined by a first captured response at which an individual can just hear a particular pure tone frequency and a second captured response at which the pure tone frequency becomes intolerably loud for the individual.

Heuristic 310 can provide a set of rules to generate respective DSP algorithm or model identifier 308 and DSP parameters 306 to correct any impairments detected in the measured minimum threshold and discomfort measurements embodied in audiological profile 202. An example heuristic 310 for mapping a set of minimum threshold measurements and discomfort level measurements to DSP algorithm or model identifier 308 and DSP parameters 306 is described in detail below. However, for purposes of the present discussion, it is sufficient to recognize that psychoacoustic model 304 can specify that a minimum threshold measurement exceeding a particular threshold (e.g., exceeding a nominal value) as a function of frequency should require an associated frequency to be boosted to compensate for the minimum threshold offset from a nominal value.

Based on this psychoacoustic model, DSP optimization model can use heuristic 310 to select a filter bank and compression algorithm or model (i.e., DSP algorithm or model identifier 308). Heuristic 310 can then indicate that frequencies at which loss is detected (i.e., minimum threshold exceeds a nominal value) should be boosted to compensate for the offset or in some proportionate manner. Heuristic 310 can be applied across a range of frequencies to calibrate the range of losses across the entire auditory spectrum. Further, heuristic 310 can further provide rules for selecting audio compressor parameters such as compressor threshold, ratio, attack, and release times based upon the minimum threshold and discomfort measurements. Heuristic 310 can further account for potential analog or digital clipping that can occur at speech level dynamics for a speech signal, which can result from the aforementioned frequency boosting and further refine the parameters to mitigate such clipping.

According to one embodiment, rather than using heuristic 310 to generate DSP algorithm or model identifier 308 and associated DSP parameters, DSP optimization component 122 can generate DSP algorithm or model identifier 308 and DSP parameters 306. As shown in FIG. 3, transfer characteristic 312 can be generated from psychoacoustic model 304. According to one embodiment, transfer characteristic 312 can include a representation of a perceptual audio path for user 216. In particular, transfer characteristic 312 can be a function that represents the operation of the ear-neural pathway on a received sonic signal.

On the other hand, optimizer 302 can use a physical model of the human auditory perception system including the physiological attributes of audio perception and the neural pathway affecting sound perception, which is based on the psychoacoustic model 304. In this context, optimizer 302 can use a linear or non-linear map that relates an input speech/audio signal to an output speech/audio signal.

DSP algorithm or model identifier 308 can include any alphanumeric or other label specifying a particular DSP algorithm or model. A DSP algorithm or model can include programmable descriptive information including, for example, a mathematical description or block diagram description of a processing operation to be performed on unprocessed audio signal 120(a). A DSP algorithm or model can operate on signals either in the time domain or frequency domain and therefore an associated transformation between the domains can be performed prior and subsequent to processing. For example, according to one embodiment, a DSP algorithm or model can separate a speech signal into various bands and then process each frequency band separately by applying boost(s) as appropriate to each respective band. A respective compressor can then process each band separately. Finally, the respective bands that have undergone boosting and compression can then be recombined and possibly passed through an audio limiter. More details of an example DSP algorithm or model are described below with respect to FIG. 5B.

For purposes of the present discussion, it is sufficient to understand that any DSP algorithm or model can be performed by processing device 102. In addition, it will be appreciated that each DSP algorithm or model will have an associated set of DSP parameters 306 that control the processing operation of the algorithm. Thus, using the previous example of a multiband boost and compression DSP algorithm, each frequency band can have an associated boost parameter as well as a set of compression parameters for that band.

In this example, the heuristic function can be provided with audiological profile 202 that represents a set of minimum threshold measurements and discomfort measurements. Optimizer 302 selects a particular DSP algorithm or model that can directly compensate for the detected minimum threshold measurements and discomfort levels specified in, for example, an audiological profile. In this case, for example, optimizer 302 can select a simple DSP algorithm or model comprising a multiband filter bank and associated set of compressors. In some instances, user 216 can further customize a DSP algorithm or model selected by the optimizer 302 by changing selected DSP algorithm or model parameters via, for example, a user interface implemented by processing device 102. In some other instances, the user 216 can select a more complex or different DSP algorithm or model than the one selected by the optimizer 302 via the user interface implemented by processing device 102.

Figure 4:
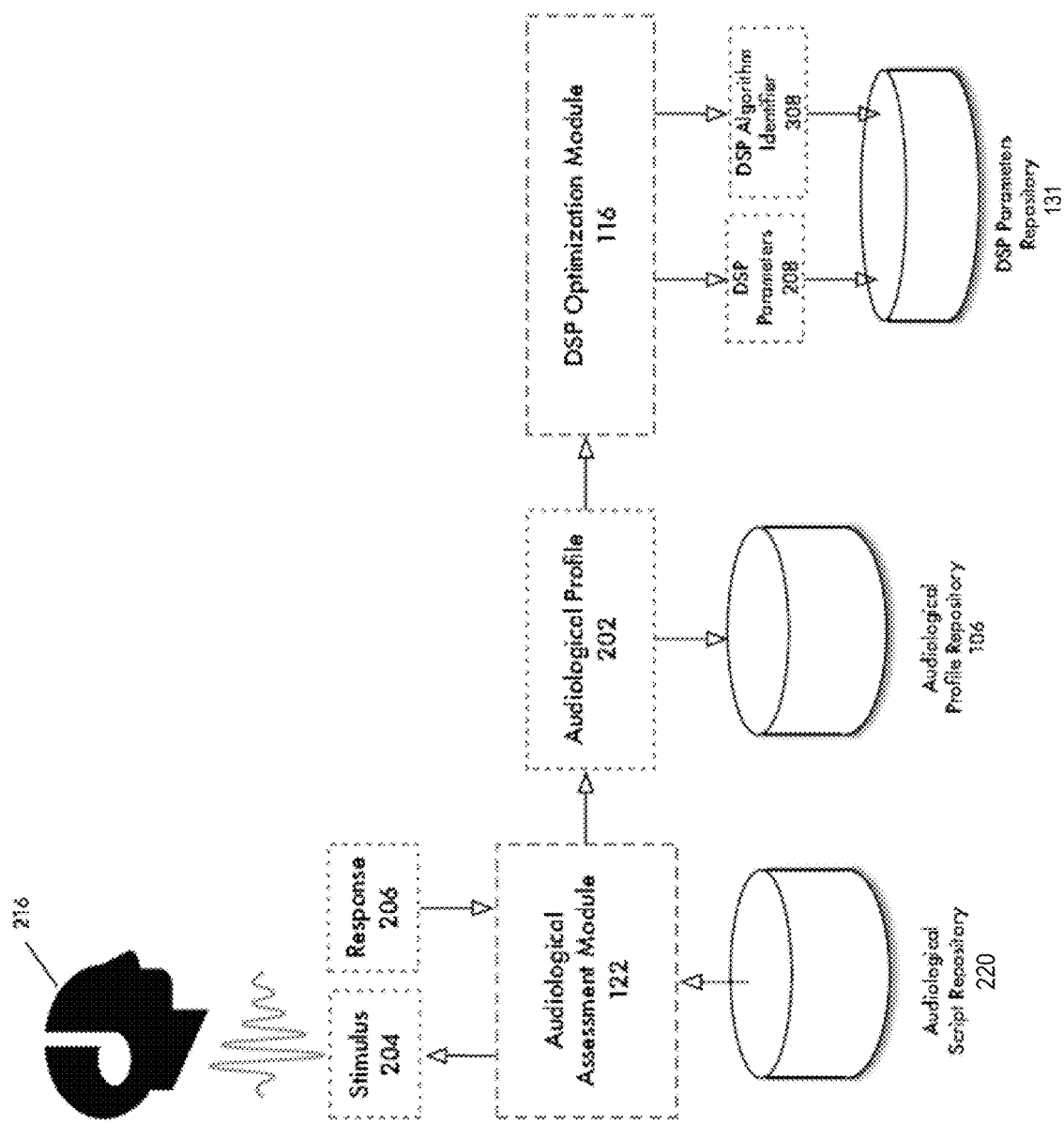
FIG. 4 is a block diagram depicting an operation of an audiological assessment component and a DSP optimization component, according to an embodiment.

While an exemplary audiological assessment scheme was described above, FIG. 4 is a block diagram depicting an operation of an audiological assessment component or component and a DSP optimization component or component according to one embodiment. For purposes of the present discussion, it is assumed that an audiological assessment is to be performed for user 216. More detailed descriptions of audiological assessment component 122, audiological profile 202, and DSP optimization component 116 are provided below. As shown in FIG. 4, audiological assessment component 122 can generate stimulus 204, which is provided to user 216. A stimulus 204 can include any information that is presented to user 216. According to one embodiment, stimulus 204 can include an audio signal such as, for example, a pure-tone frequency. According to alternative embodiments, stimulus 204 can include a more complex audio signal such as an audio signal generated by sweeping across a range of frequencies. According to other embodiments, stimulus 204 can include a multimedia signal comprising a mixture of media types including, for example, audio and visual signals.

In response to receiving and perceiving stimulus 204, user 216 can then provide response data 206. Response data 206 can include any information or data represented in digital form. Response data 206 can be provided by any mechanism through which user 216 can interact with a digital computer. For example, according to one embodiment, individual 206 can provide response data 206 by interacting with a UI element that can be presented on a screen associated with processing device 102. According to alternative embodiments, user 216 is not requested to perform an affirmative action but instead a detector or a sensor (not shown in FIG. 4) that detects some attributes related to user 216 or the environment surrounding user 216 can generate response data 206. For instance, processor 108 can receive a signal from a sensor included in compute device 102, and/or transceiver 108 indicating that the environmental conditions surrounding user 216 have changed. Thus, processing device 102 can adapt or replace a DSP model currently used by user 216 such that, the adapted or new DSP model compensates for any loss of hearing or discomfort that can result from environmental changes. Audiological assessment component 122 can then receive response data 206 from user 216 based on individual's degree of perception of stimulus 204.

Figure 5A:
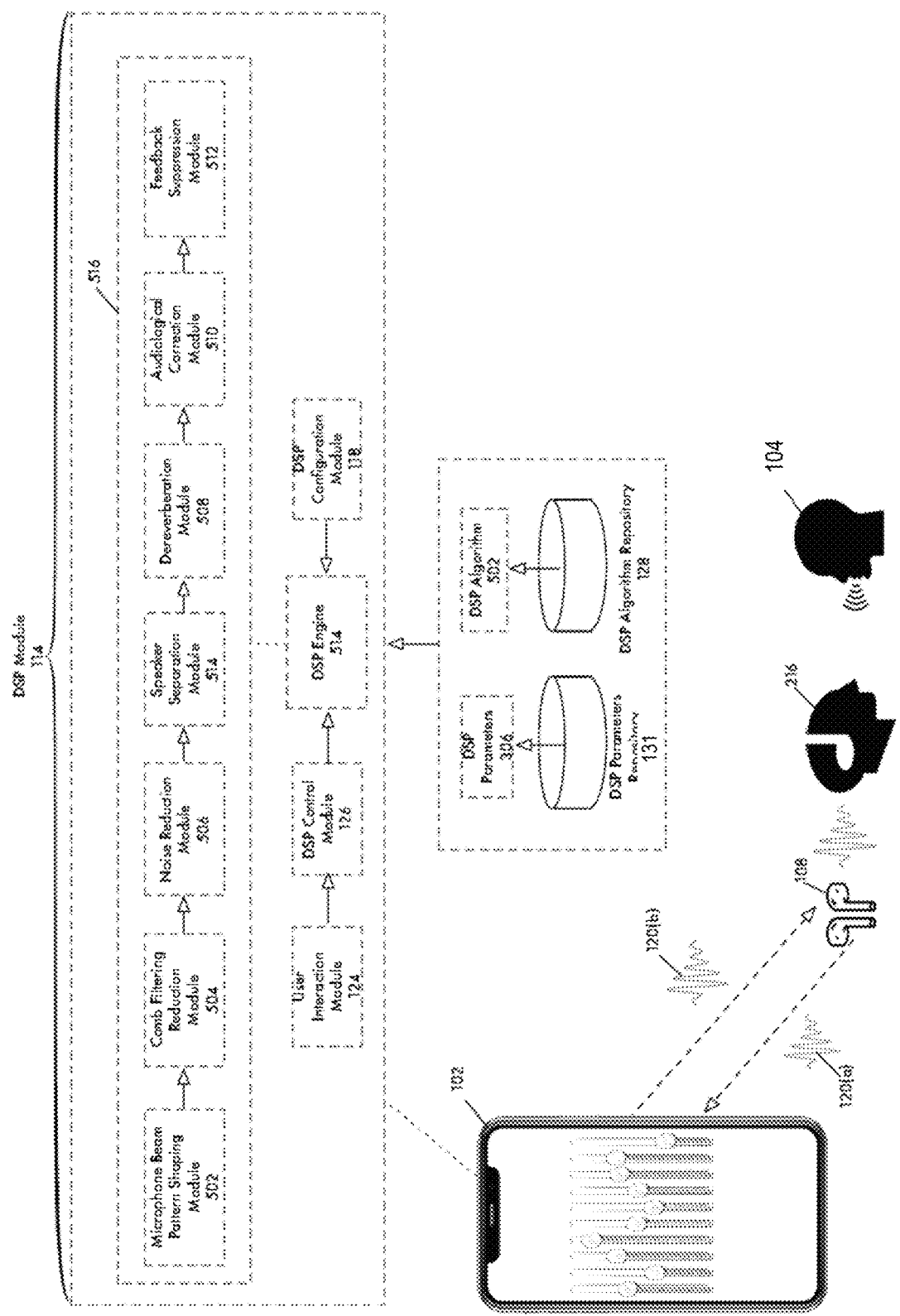
FIG. 5A depicts a structure and operation of a DSP component, according to an embodiment.

FIG. 5 depicts a structure and operation of a DSP, according to one embodiment of the present disclosure. DSP component 114 can perform audio processing of unprocessed audio 120(a) received from transceiver device 108 to generate processed audio 120(b) to correct a particular audiological profile 202 of user 216. As shown in FIG. 5, DSP component 114 can further include DSP processing elements 516, user interaction component 124, DSP control component 126, DSP configuration component 118 and DSP engine 114. The elements comprising DSP component 114 can be software components that execute on a CPU. Alternatively, one or more of the elements shown in FIG. 5 can include a dedicated hardware component. Details regarding possible embodiments are described below.

DSP engine 114 performs transformation of unprocessed audio 120(a) to processed audio 120(b). As shown in FIG. 5, DSP processing elements can further include microphone beam pattern shaping component 502, comb filter reduction component 504, noise reduction component 506, dereverberation component 508, audiological correction component 510 and feedback suppression component 512. According to some embodiments, only a portion of processing elements 502-514 can be present. For example, according to one embodiment, only noise reduction component 506, audiological correction component 510 and feedback suppression component 512 can be present. Any other combination is possible.

Figure 5B:
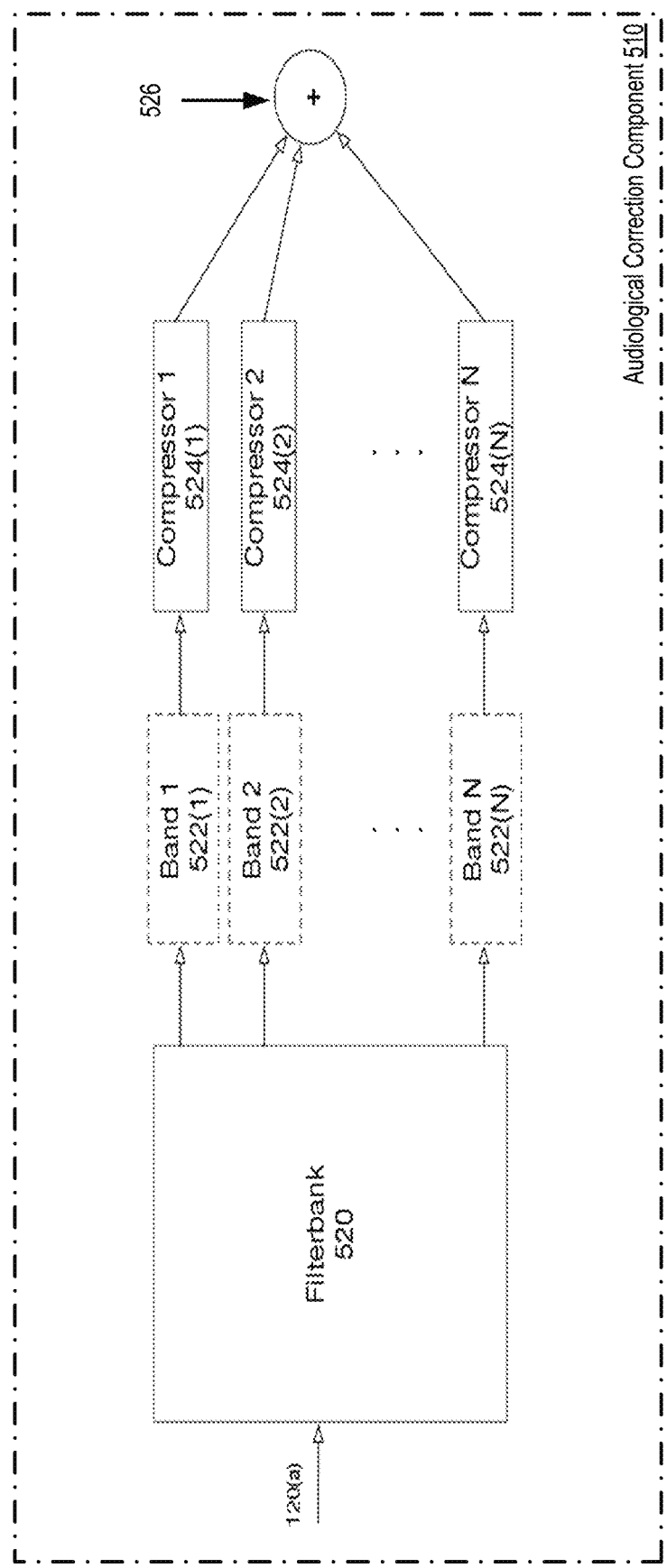
FIG. 5B depicts a structure and operation of an audiological correction component, according to an embodiment.

Attention is drawn to FIG. 5B showing sub-components of audiological correction component 510. In some implementations, the audiological correction component 510 receives an unprocessed audio signal 120(a) which is pass through filter bank 520. Filter bank 520 can be a multiband filter bank associated set of compressors. Accordingly, in some implementations, filter bank 520 separates the unprocessed audio signal 120(a) into multiple bands, each band (522(1), 522(2) . . . 522(N)) carrying a single frequency sub-band of the unprocessed audio signal 120(a). Compressor 524(1), 524(2), . . . 524(N) process each band (522(1), 522(2) . . . 522(N)) boosting and/or compressing bands which are later recombined at 526.

Figure 5C:
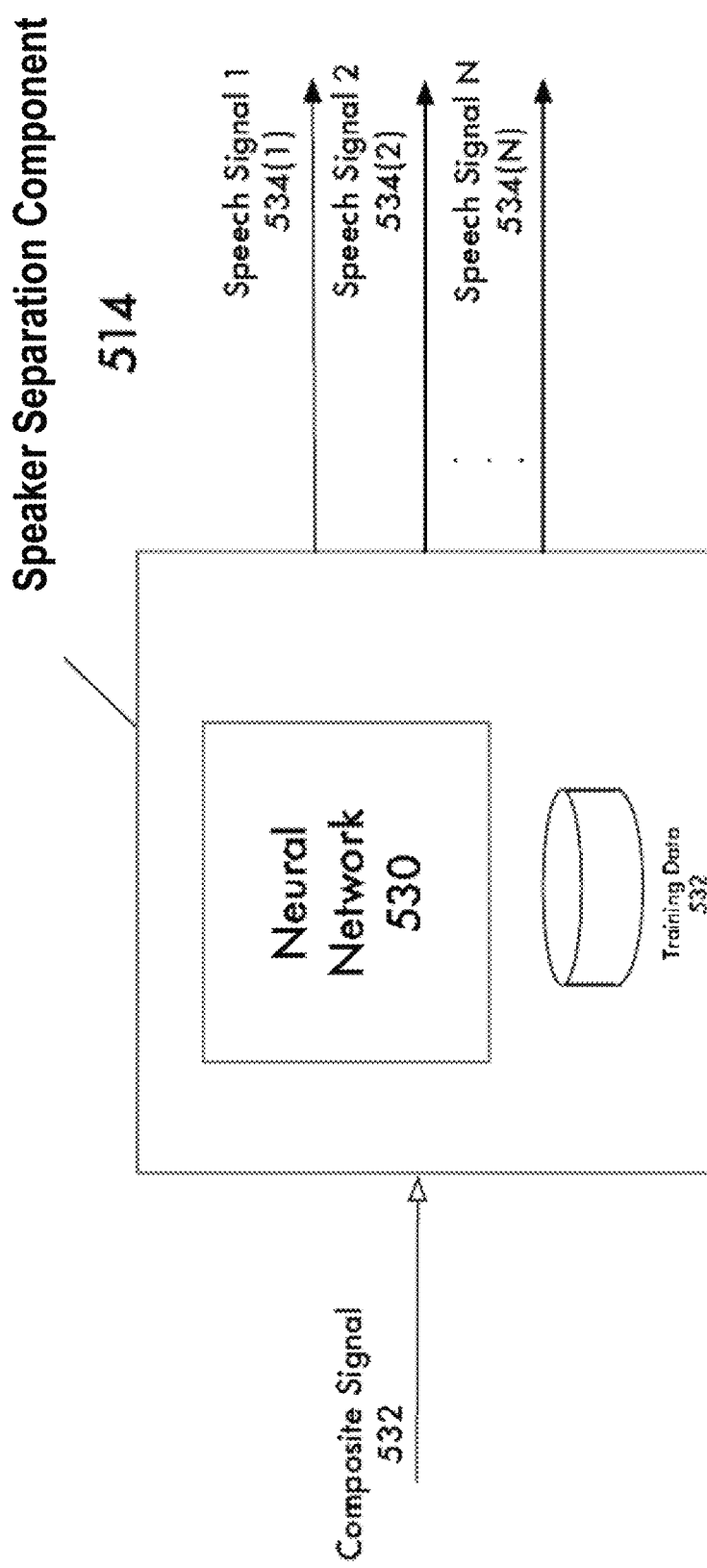
FIG. 5C depicts a structure and operation of a speaker separation component, according to an embodiment.

FIG. 5C shows an example of a speaker separation/segmentation component 514 implemented with a neural network 530. In some implementations, the speaker separation/segmentation component 514 separates the voice signal of a user of the mobile compute device from a speaker's voice. Accordingly, each of the speech signals 534(1), 534(2), . . . 534(3) can include either speech signal corresponding to the user of the mobile compute device or a speech signal of the speaker's voice (different from the voice signal of the user). Thus, the neural network 530 can a pre-trained neural network configured to discern between the user's voice signal and a speaker's voice signal. In some instances, the neural network 530 can be trained and/or retrained with training data stored at repository 532. It is appreciated that the neural network 530 can separate voice signals from two or more simultaneous speakers with no prior knowledge of such speakers. More specifically, the neural network 530 can separate the voice signals from the user of the mobile compute device and, for example, voice signals from other speakers different form the user of the mobile compute device.

Reflexive Voice Correction

Utilizing a mobile compute device or other general processing to operate as a Personal Sound Amplification Product (PSAP) or hearing aid device can be sub-optimal because in addition to receiving speaker's voices in the ambient environment for processing, the voice of the individual/user 216 will also be received by the microphones, processed and then played back to user 216. Because user 216 is in closer proximity to the microphones, his/her voice signal will typically be much louder than the voice signals of other speakers in the ambient environment. In particular, if user 216 uses a wireless headset with built-in microphones, those microphones can be located close to individual's mouth and can be designed to perform some type of beamforming to focus the microphone beam pattern at the individual's mouth as the intention of such devices is to pick up a speech signal for telephony, not for recording and processing and ambient acoustic space. Combined with the latency that will be introduced due to processing block size, coding delays, processing delays, and transmission delays, the effect of user 216 hearing his/her own voice processed and played back to him/her is highly undesirable.

Figure 6:
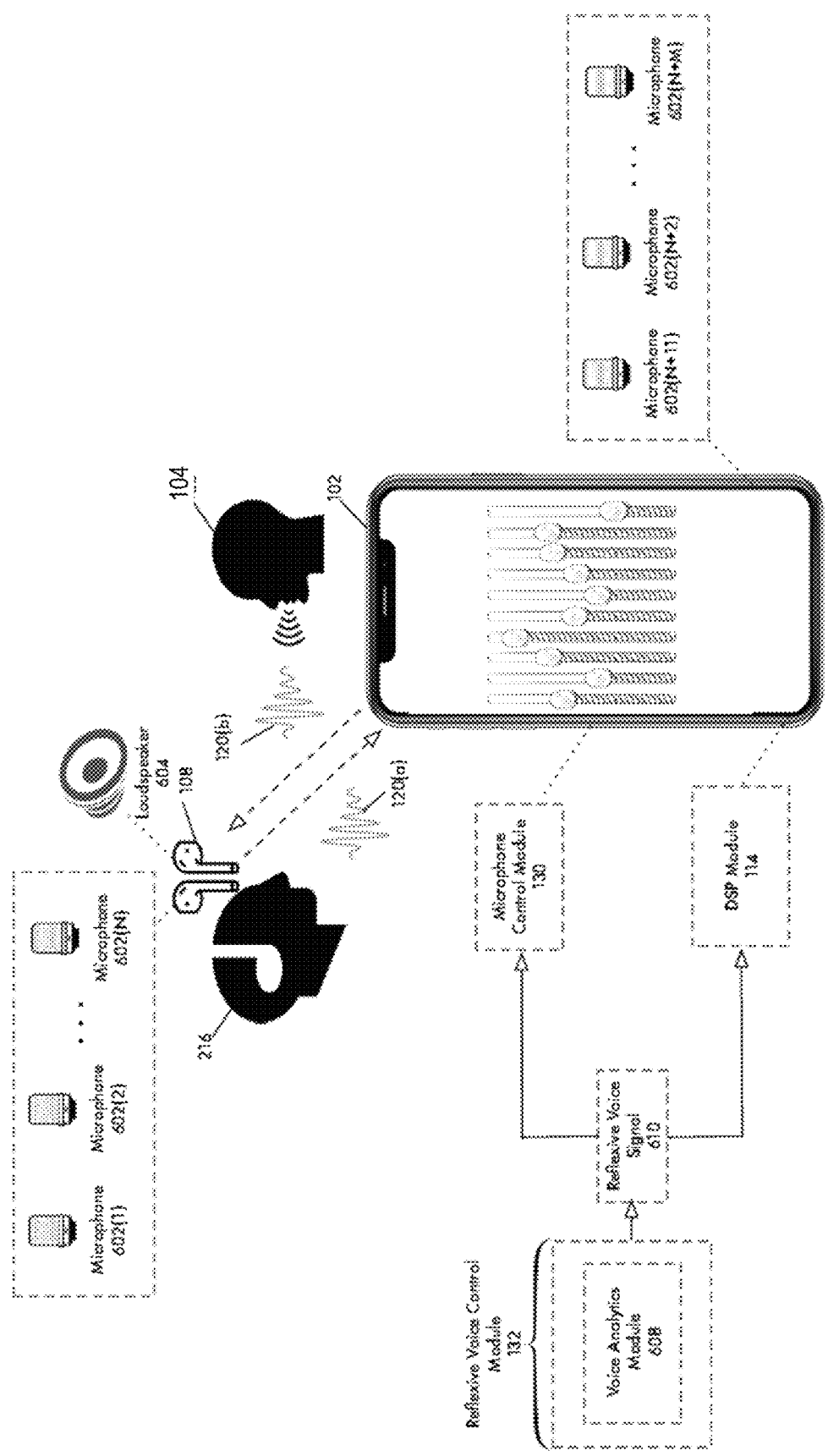
FIG. 6 is a block diagram with an example solution to a reflexing voice problem, according to an embodiment.

This problem is referred to herein as a reflexive voice problem. Referring now to FIG. 6, the effects of the reflexing voice problem will now be described in more detail. User 216 will also typically generate a voice signal in order to communicate back to the speaker 104. That individual's voice will then also be processed by DSP component 114 and played back to user 216, which can be undesirable for several reasons. First, because user 216 is close in proximity to microphones 602(1)-602(N) associated with transceiver device 108, the individual's voice will be very loud when detected by microphones 602(1)-602(N) in comparison to the other speaker's voice (e.g., speaker 104 in FIG. 5). Second, due to the latency of processing individual's voice, there can be a noticeable delay between the time user 216 speaks and when user 216 hears his/her played-back voice signal, which can be disorienting to user 216. In addition, in general, user 216 will hear his/her own unprocessed voice signal as well as his/her processed voice signal resulting in interference between the processed audio signal 120(b) and the ambient acoustic signal entering individual's ears. The unprocessed and processed voice signals associated with user 216 will therefore be mixed, but in an undesirable manner that can result in user 216 hearing his/her voice with significant coloration that can also be disorienting. For purposes of the present discussion, a reflexive voice condition exists when the user 216 is speaking. In some instances, detecting such a condition is complicated because the individual's voice that should trigger the reflexive voice condition and not the presence of other voices in the ambient environment.

Reflexive voice control component 132 (shown in FIG. 6) can operate to mitigate or eliminate the effects of the reflexive voice problem. In particular, as described below, according to one embodiment, reflexive voice control component 132 can operate to detect whether a reflexive voice condition exists and perform appropriate corrective action.

FIG. 6 depicts a structure and operation of a reflexive voice control component in conjunction with microphone control component 130 according to one embodiment of the present disclosure. Speaker 104 generates a voice signal (120(b)) that is received by one or more microphones 602(1)-602(N) on transceiver device 108 (as unprocessed audio 120(a)) and/or one or more microphones 602(N+1)-602(M) on processing device 102 and processed by DSP component 114 executing processing device 102 to generate processed audio 120(b). Processed audio 120(b) is then played back to user 216 via loudspeaker 604 on transceiver device 108, for example. Although FIG. 6 shows only a single speaker 104, it will be understood that there can be multiple speakers 104 communicating with user 216.

Reflexive voice control component 132 operates to mitigate and/or eliminate the effects of the reflexive voice problem associated with user 216 hearing his/her own voice as detected by microphones 602(1)-602(N) or microphones 602(N+1)-602(M). Microphone control component 130 can operate to control which microphones 602(1)-602(N) and 602(N+1)-602(N+M) are selected and operational at any given time. For example, microphone control component 130 can cause only microphones 602(1)-602(N) to be on while simultaneously causing microphones 602(N+1)-602(N+M) to be off.

In particular, reflexive voice control component 132 can send various control signals to microphone control component 130 and/or DSP component 114 (i.e., reflexive voice signal 610) to correct the existence of reflexive voice condition. According to one embodiment, reflexive voice control component 132 can further include voice analytics component 608. Voice analytics component 608 can operate to detect that user 216 is currently speaking. According to one embodiment, voice analytics component 608 can analyze the dynamics of signals detected by microphones 602(1)-602(N) and microphones 602(N+1)-602(N+M) to determine whether user 216 is currently speaking. An example of a process performed by voice analytics component 608 to determine whether user 216 is currently speaking is described below with respect to FIG. 5B-5C. According to an alternative embodiment, voice analytics component 608 can perform a speaker classification process to determine whether user 216 is speaking or not. According to yet another embodiment, DSP component 114 can perform a speaker segmentation process or technique using speaker segmentation component 514 to separate individual's voice from speaker's voice. In such a case, only the speaker's voice compensated according to the individual's impairment is played back to the individual and not his/her own voice.

Upon detecting that user 216 is speaking, reflexive voice control component 132 can send appropriate signals (i.e., reflexive voice signal 610) to microphone control component 130 to cause the muting of one or more microphones 602(1)-602(N) and 602(N+1)-602(M+1).

Figure 7A:
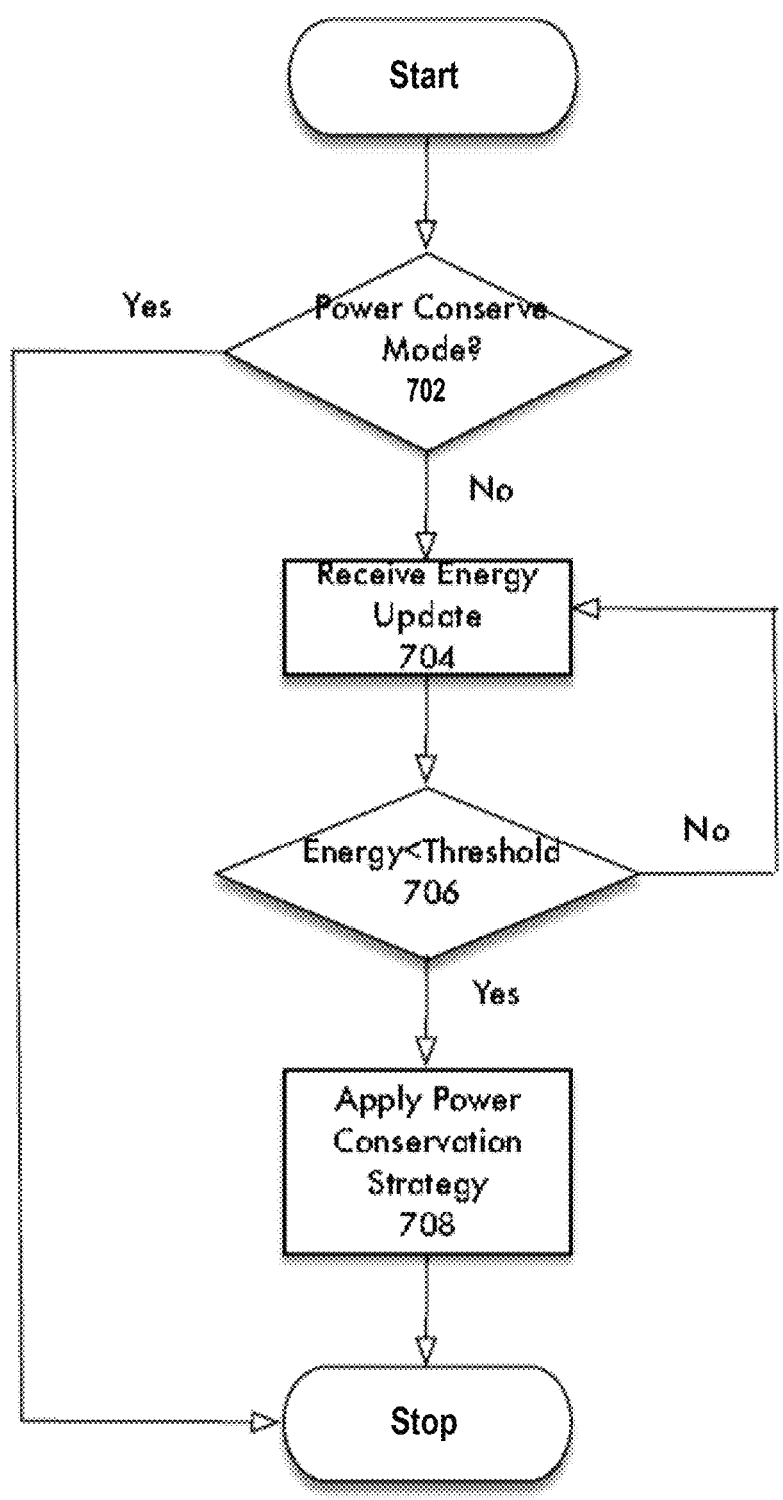
FIG. 7A-7C depict a structure and operation of a power management component, according to an embodiment.

FIG. 7A depicts an operation of a power management component according to one embodiment of the present disclosure. According to various embodiments of the present disclosure, the power management component monitors the power levels of a mobile compute device. In some instances, when the power management component detects that the power or energy level of the mobile compute device is falling below a predetermined threshold, the power management component causes the device based hearing enhancement processes to enter a power conservation mode. As described below, according to one embodiment of the present disclosure, in a power conservation mode various DSP processes can be shut down or modified to consume lower power and thus, conserving energy of the mobile compute device.

In some instances, the power management component determines whether the power conserve mode is active. If so ('Yes' branch at 702), the process ends in 710. If not ('No' branch at 702), the flow continues with 704 whereby an energy update is received. According to one embodiment of the present disclosure, an energy update may be received by invoking an API call associated with the operating system of the mobile compute device which responds with the energy or power levels of a mobile compute device. At 706, a conditional statement is executed to determine whether the current energy available on the mobile compute device falls below a threshold. If so ('Yes' branch at 706), the flow continues at 708 where a power conservation strategy is invoked. Some examples of power conservation strategies are described below with respect to FIGS. 7B-7C. In some instances when the energy or power level of the compute device is not below the predetermined threshold ('No' branch of 706), the flow continues at 704 and where a new energy update is received.

Figure 7B:
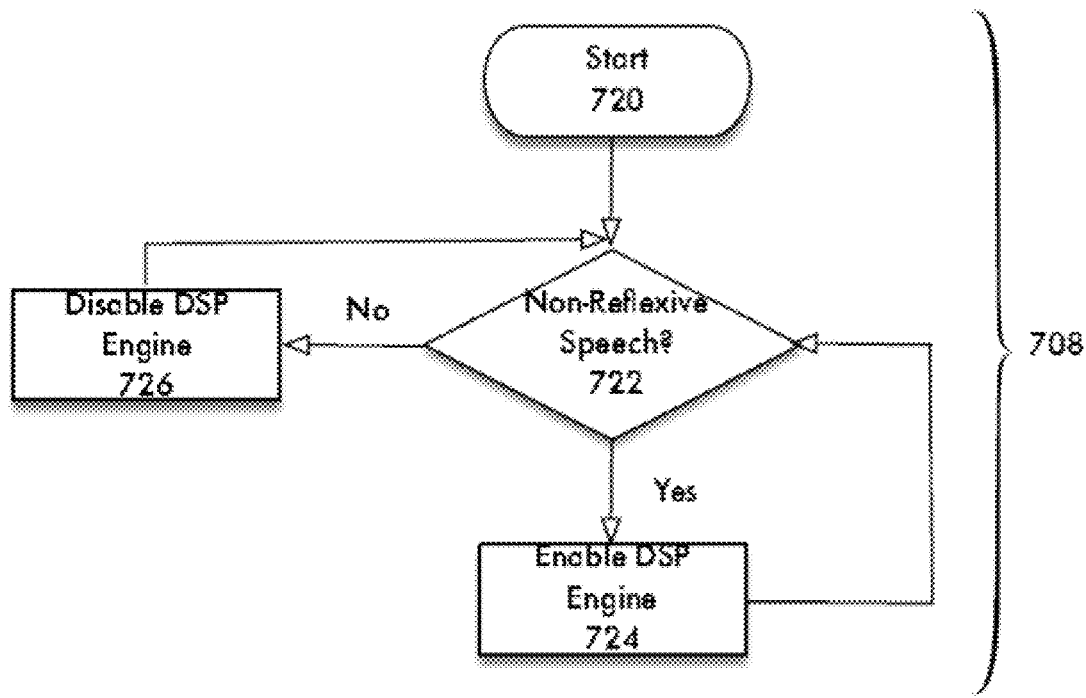

FIG. 7B is a flowchart depicting a power conservation strategy. The process shown in FIG. 7B is an example of a power conservation strategy that can be invoked at 708 discussed with reference to FIG. 7A. In some instances, the power conservation strategy shown in FIG. 7B detects via conditional statement 722 whether incoming audio is non-reflexive speech. In some instances, when it is determined that the incoming audio is non-reflexive speech (e.g., speech from an external subject) the DSP engine 114 is enabled at 724. If no speech is present or the speech is reflexive, then the DSP engine 114 is disabled at 726. An example of a technique for detecting non-reflexive speech is described above with reference to FIG. 5C including a deep machine learning technique utilized to detect the subject's voice. Alternatively, the volume level of the incoming speech can be analyzed.

Figure 7C:
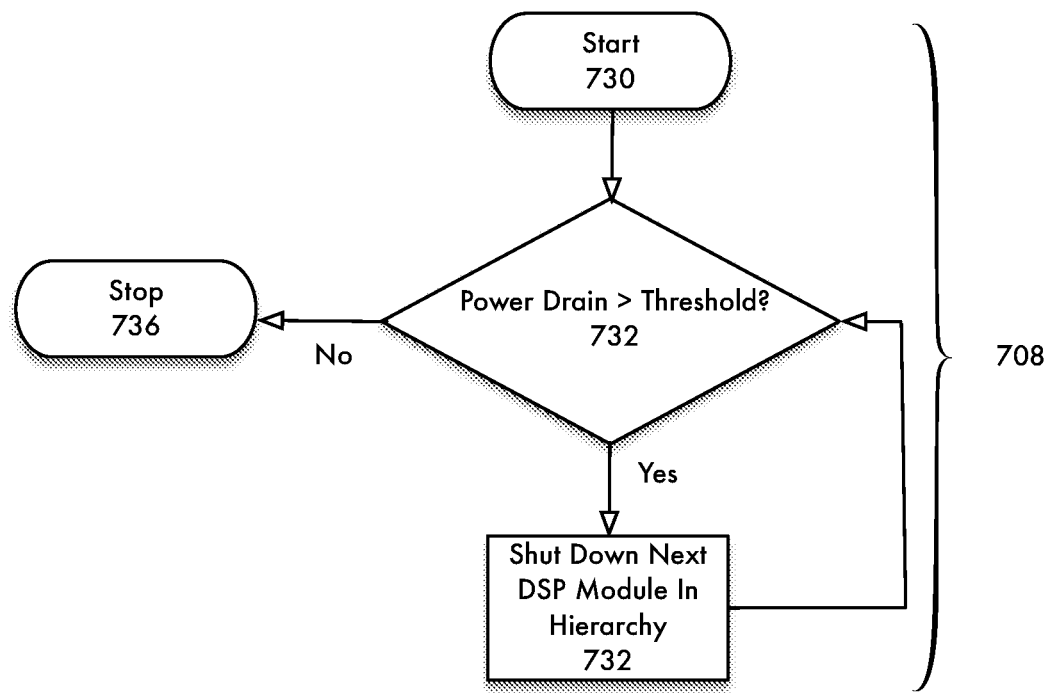

FIG. 7C is a flowchart depicting a power conservation strategy. In some instances, the power conservation strategy shown in FIG. 7C detects a current power drain parameter. If the power drain parameter exceeds a pre-determined threshold, various components performed by the DSP engine are selectively disabled. According to one embodiment of the present disclosure, each DSP component executing a DSP process can be analyzed to determine its contribution to the power drain as well as other attributes such as whether the DSP component is essential to the overall DSP processes. In particular, a DSP process can comprise multiple DSP sub-processes executed by more than one DSP component, some of these DSP sub-processes may not be essential for operation of the overall DSP process. The non-essential DSP sub-processes drawing the most power can then be selectively disabled in an iterative fashion. The DSP components can be arranged in a hierarchical fashion based upon the amount of power each DSP component utilizes or consumes.

The process shown at FIG. 7C determines at 732, whether the current power drain exceeds a predetermined threshold. If not ('No' branch at 732), the flow continues at 736 and the process ends. If the power drain exceeds the predetermined threshold ('Yes' branch at 732), the next DSP component in the hierarchy or arrangement of non-essential DSP components is shut down at 734. Flow then continues at 732 where it is again determined whether the current power drain exceeds a predetermined threshold.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made. Additionally, certain of the steps may be performed concurrently in a parallel process when possible, as well as performed sequentially as described above. Although various embodiments have been described as having particular features and/or combinations of components, other embodiments are possible having any combination or sub-combination of any features and/or components from any of the embodiments described herein. Furthermore, although various embodiments are described as having a particular entity associated with a particular compute device, in other embodiments different entities can be associated with other and/or different compute devices.

It is intended that the systems and methods described herein can be performed by software (stored in memory and/or executed on hardware), hardware, or a combination thereof. Hardware components may include, for example, a central processing unit, a field programmable gates array (FPGA), and/or an application specific integrated circuit (ASIC). Software components (executed on hardware) can be expressed in a variety of software languages (e.g., computer code), including Unix utilities, C, C++, Java™, JavaScript, Ruby, SQL, SAS®, Python, Fortran, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code. Each of the devices described herein can include one or more processors as described above.

The invention claimed is:

1. An apparatus, comprising:
a processor;
a source device, and
a memory storing code which, when executed by the processor, causes the processor to:
produce a set of audiological assessment data based on a set of stimulus signals presented to a user via the source device and a set of response signals provided as a response to the set of stimulus signals;
identify a personal audiological profile of the user at least based on a psychoacoustic model representing speech discrimination and the set of audiological assessment data;
select a set of audio digital signal processing functions coded in the memory based on the personal audiological profile and a set of heuristics coded in the memory;
build a digital signal processing model that includes the set of audio digital signal processing functions and addresses said personal audiological profile;
upon determining that the user is speaking, execute the digital signal processing model to produce an output audio signal in response to an input audio signal received from the source device, the output audio signal is based on a modified version the input audio signal and adjusted with said personal audiological profile such that a voice of the user is not amplified in the output audio signal; and
transmit the output audio signal via the source device.

2. The apparatus of claim 1, wherein the code to produce the set of audiological assessment data, further causes the processor to:
play the set of stimulus signals to the user via the source device; and
receive at the processor, the set of response signals, each response signal from the set of response signals associated with a stimulus signal from the set of stimulus signals, and associated to the user level of perception of that stimulus signal.

3. The apparatus of claim 1, wherein the code to select the set of audio digital signal processing functions, further causes the processor to:
determine a set of digital signal processing parameters based on the personal audiological profile and the set of heuristics, each digital signal processing parameter from the set of digital signal processing parameters associated with at least one audio digital signal processing function from the set of audio digital signal processing functions.

4. The apparatus of claim 1, wherein the code to transmit the output audio signal via the source device include code to:
play the output audio signal at the source device.

5. The apparatus of claim 1, wherein the source device includes at least one microphone and the memory storing code which, when executed by the processor, further causes the processor to:
mute the at least one microphone upon the determination that the user is speaking.

6. The apparatus of claim 1, wherein the digital signal processing model includes an audiological correction component with a filter bank component and a set of compressor components, the filter bank component configured to separate the input audio signal into a set of frequency bands and each compressor component from the set of compressor components configured to process a frequency band separately by applying a boost value to address the identified hearing impairment.

7. The apparatus of claim 1, wherein the audiological profile includes a set of minimum threshold measurements and discomfort measurements associated with the user.

8. The apparatus of claim 1, wherein the source device includes at least one of a microphone, a speaker, and a transceiver.

9. A non-transitory computer-readable medium comprising code which, when executed by a processor, cause the processor to:
identify a user hearing impairment based on a set of stimulus signals sent to a user via a mobile compute device and a set of signals provided as a response to the set of stimulus signals;
select a set of parameters of a digital signal processing model based, at least in part on the identified user hearing impairment and a transfer characteristic based on a psychoacoustic model;
determine a set of values for each parameter from the set parameters based on the identified hearing impairment and the transfer characteristic;
upon determining that the user is speaking, execute the digital signal processing model configured to take as input the set of values determined for each parameter from the set of parameters and produce an output audio signal, the output audio signal produced in response to an input audio signal received at the mobile compute device, the output audio signal excluding a processed component corresponding to the user's speech; and
transmit via the mobile compute device, the output audio signal.

10. The non-transitory computer-readable medium of claim 9 wherein the set of values determined for each parameter from the set of parameters includes a boost value associated with a frequency band.

11. The non-transitory computer-readable medium of claim 9 wherein the set of values determined for each parameter from the set of parameters includes a value of an audio compression attribute.

12. The non-transitory computer-readable medium of claim 9 wherein the digital signal processing model includes an audiological correction component with a filter bank component and a set of compressor components, the filter bank component configured to separate the input audio signal into a set of frequency bands and each compressor component from the set of compressor components configured to process a frequency band separately by applying a boost value to address the identified hearing impairment.

13. The method of claim 12, wherein the source device includes at least one of one of a microphone, a speaker, and a transceiver.

14. A method comprising:
producing at a processor, a personal audiological profile based on a set of stimulus signals emitted to a predetermined user via a source device coupled to the processor and a set of signals provided as a response to the set of stimulus signals;
selecting, based on the personal audiological profile a digital signal processing model from a set of digital signal processing models stored in a memory coupled to the processor;
determining whether a reflexive voice condition exists, the reflexive voice condition existing when the predetermined user is speaking,
when the reflexive voice condition exists, produce an output audio signal configured to be heard by the predetermined user, a voice of the predetermined user not being processed in the output audio signal; and
executing the digital signal processing model to produce the output audio signal by modifying an input audio signal received from the source device when the reflexive voice condition does not exist.

15. The method of claim 14, wherein the transceiver includes at least one microphone and the method further comprises:
sending a signal to mute the at least one microphone when it is determined that the reflexive voice condition exists.

16. The method of claim 14, wherein, when the reflexive voice condition exists, executing the digital signal processing model by extracting, via a neural network, a component of the input audio signal corresponding to the predetermined user's voice such that the output audio signal does not include a component corresponding to the predetermined user's voice.

17. The method of claim 14, wherein the audiological profile includes a set of minimum threshold measurements and discomfort measurements associated with the predetermined user.

18. The method of claim 14, wherein the input audio signal is received from at least one microphone coupled to the processor.

* * * * *